(12) United States Patent
Davankov

(10) Patent No.: US 6,497,675 B1
(45) Date of Patent: Dec. 24, 2002

(54) DEVICE FOR EXTRACORPOREAL TREATMENT OF PHYSIOLOGICAL FLUIDS OF ORGANISM

(75) Inventor: Vadim Davankov, Moscow (RU)

(73) Assignee: Renal Tech International LLC, New York, NY (US)

( * ) Notice: Subject to any disclaimer, the term of this patent is extended or adjusted under 35 U.S.C. 154(b) by 0 days.

(21) Appl. No.: 09/529,751

(22) Filed: Apr. 17, 2000

(51) Int. Cl.[7] ................ A61M 37/00; B01D 35/00; B01D 39/00; B01D 61/00
(52) U.S. Cl. ............... 604/6.09; 604/4.01; 604/5.01; 604/5.04; 210/433.1; 210/434; 210/501; 210/502.1; 210/644; 210/645; 210/650; 210/651
(58) Field of Search ................ 604/4.01, 5.01, 604/6.01, 6.09; 210/348, 407, 433.1, 434, 435, 500.23, 501, 502.1, 504, 646, 650, 506

(56) References Cited

U.S. PATENT DOCUMENTS

| | | | |
|---|---|---|---|
| 4,000,072 A | * 12/1976 | Sato et al. ................. 210/315 |
| 4,140,652 A | 2/1979 | Korshak |
| 4,609,461 A | * 9/1986 | Takata et al. ............. 210/195.2 |
| 5,151,082 A | 9/1992 | Gorsuch |
| 5,194,157 A | 3/1993 | Ghezzi |
| 5,211,850 A | * 5/1993 | Shettigar et al. ............. 220/3.5 |
| 5,286,449 A | * 2/1994 | Kuroda et al. .............. 210/490 |
| 5,536,412 A | 7/1996 | Abe |
| 5,773,384 A | 6/1998 | Davankov |
| 5,855,782 A | * 1/1999 | Falkenhagen et al. ... 210/195.2 |
| 6,022,477 A | * 2/2000 | Luo et al. ................... 210/645 |
| 6,287,516 B1 | * 9/2001 | Matson et al. ............. 210/650 |

OTHER PUBLICATIONS

The Concept of Sorbents in Hemodialysis Int. Journ. of Artificial Organs pp 305–308, 1998.

* cited by examiner

Primary Examiner—Angela D. Sykes
Assistant Examiner—Leslie R. Deak
(74) Attorney, Agent, or Firm—I. Zborovsky

(57) ABSTRACT

A device for extracorporeal treatment of physiological fluids of organism has means forming a filtration membrane for filtering smaller-size components of a physiological fluid withdrawn from a patient from larger-size components of the same, a bed of particulate adsorbing material with which the smaller-size components are contacted for purification, and means for combining the purified smaller-size components of the fluid with the larger-size components of the fluid for returning the thusly treated fluid to a patient.

13 Claims, 1 Drawing Sheet

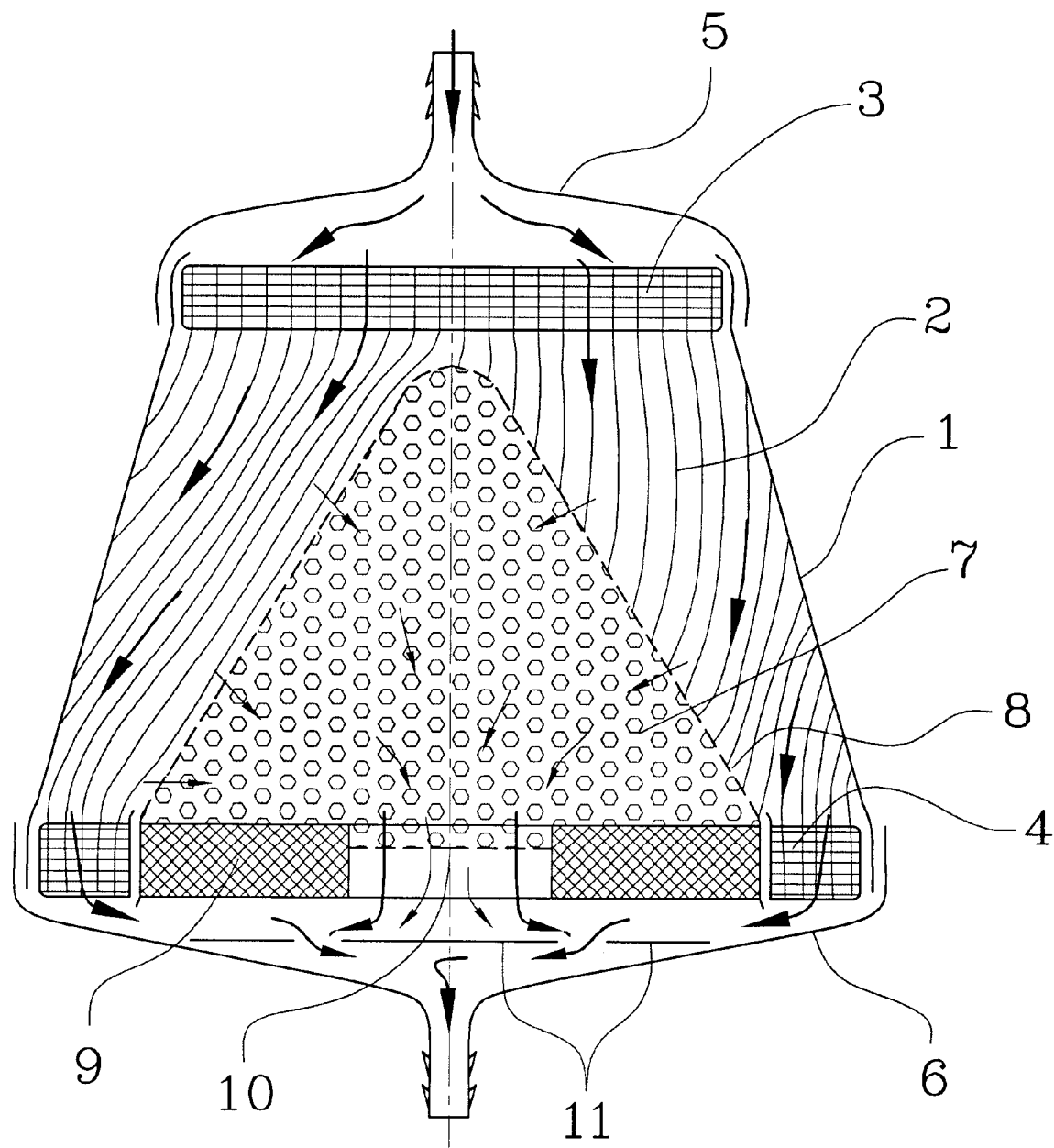

DEVICE FOR EXTRACORPOREAL TREATMENT OF PHYSIOLOGICAL FLUIDS OF ORGANISM

BACKGROUND OF THE INVENTION

The present invention relates generally to devices for extracorporeal treatment of physiological fluids of organism, in particular, a hemoperfusion device for blood detoxification.

Dialysis is a commonly used physical treatment that removes excess water, electrolytes, urea and toxins from a patients physiological fluid. It is known to perform dialysis by passing physiological fluids such as blood along one side of a dialysis membrane and a special dialysate liquid along the other side. The known dialysis membranes are generally permeable to small molecular weight components of solutions and these components, by diffusing through the membrane, are exchanged between the above two liquids. Toxic metabolites of the physiological fluid, after passing the membrane, can thus be removed from the organism by the flow of the dialysate liquid. However, diffusion is a relatively slow process, so that 3 to 4 hours are needed for a sufficient clearance of blood. Moreover, the removal of larger toxic components from blood, the so called "middle molecular weight toxins", is much too slow, if possible at all, by the technique, because even the modern high permeable membranes used for hemodialysis must have a cut-off below 40–50 kD. This technique is useless if large toxic compounds are needed to be removed from the physiological fluid, such as endotoxins or tissue destruction products. In some acute cases of poisoning or drug overdose, the hemodialysis technique can prove to be too slow, as the diffusion of toxins trough the membrane would require such a long time, that would make the whole treatment impractical. Another disadvantage of the hemodialysis treatment is that it requires a complicated and expensive equipment and highly skilled medical personal and, therefore, cannot be quickly provided in emergency situations outside an adequate medical institution.

A much faster technique for removing unwanted compounds from a physiological fluid is the adsorption. It is known to pass the blood through a cartridge with activated carbon or polymeric adsorbent. Such a hemoperfusion treatment can be very efficient for rapid removing of both small and middle molecular weight toxins from blood or plasma. With the recent development of adsorption technologies, extremely efficient selective and non-selective polymeric adsorbing materials become available. The drawback of this technique is that highly efficient adsorbing materials are generally not hemocompatible. They quickly cause a series of adverse reactions of biological systems, complement activation and, finally, clotting of blood.

In order to enhance the biocompatibility, the adsorbing materials have to be chemically modified. Usually, polar functional groups or hemocompatible polymeric chains are introduced onto the surface of polymer beads, as suggested for example in U.S. Pat. No. 5,773,384 by Davankov et al. (1998). Korshak et al. in U.S. Pat. No. 4,140,652, (1978) suggested binding and cross-linking human serum albumin on the surface of a polystyrene-type adsorbing material. All these coverings, however, dramatically reduce the rate of mass transfer, slow down the adsorption process, diminish the adsorption capacity of the material in a reasonable period of time available for the patient treatment. Needless to say that any additional chemical treatment of the base adsorbing material increases its prize.

The above high requirements to the hemocompatibility of the adsorbing materials can be reduced significantly if blood cells and especially platelets and white blood cells are prevented from contacting directly the surface of the adsorbent. In other words, after separating cellular material of blood by some kind of hemofiltration, the remaining plasma can be quickly detoxificated with an efficient and inexpensive sorbent material.

Several kinds of continuous hemofiltration have been suggested. Gorsuch and Atkin (U.S. Pat. No. 5,151,082, 1992) suggest hollow fiber hemofiltration membranes to be surgically introduced into patients veins, in order to take plasma, instead of the whole blood, for the subsequent extracorporeal treatment.

Another procedure and device is also known, as disclosed for example in the article "The Concept of Sorbents in Hemodialysis", published in "The International Journal of Artificial Organs" volume 21, no. 6, 1998, pages 303–308. In this procedure a device is proposed which includes a hemofilter, a bioseparator and a hemodialyzer. The hemofilter separates the blood, so as to retain the blood cells and allow passage of a liquid component of the blood. The liquid component of the blood is supplied to the bioseparator which accommodates charcoal or adsorbing resin and is purified there, and then the purified liquid component together with the cells are supplied into the hemodializer. A similar system consisting of three separate units, a hemofiltration cartridge, a plasmaperfusion unit, and a hemodialyser, was earlier described in U.S. Pat. No. 5,194,157 (1993) by Ghezzi et al.

A complicated system, that allows a simultaneous combination of dialysis and filtration procedures, is subject of U.S. Pat. No. 5,536,412 (1996) by Abe et al. Here, blood is allowed to flow along one side of a membrane, whereas a suspension of a fine dispersed adsorbing material in a dialysate liquid is pumped, in a pulsation-type flow, along the other side of the membrane. Because of alternating pressure and vacuum, a very intense exchange of liquids through the membrane is accomplished.

All these systems are too complicated to be applied in a short period of time. Besides, they require a very substantial amount of blood to be involved into extracorporeal circuits, which is difficult to be tolerated by the patient.

An original compact plasma filter—sorbent system was suggested by Shettigar et al. (U.S. Pat. No. 5,211,850, 1993). Here, blood is pumped through a hollow fiber membrane-type hemofilter, that is placed into a closed chamber filled with adsorbing material. Plasma is supposed to filtrate into the chamber from the initial portion of the fibers, interact with the sorbent in the chamber and be resorbed through the same membrane in the second part of the fibers. This device minimizes the amount of blood involved into processing and provides an efficient contact between the filtrate, i.e., plasma with the polymer sorbent. A serious disadvantage of such a close device, however, is that it is impossible to observe the movement of the fluids within the device and regulate the flows. Moreover, it is difficult to distribute the adsorbent between the hollow fibers and impossible to separately regenerate and reuse the membrane and the adsorbent material.

SUMMARY OF THE INVENTION

Accordingly, it is an object of present invention to provide devices for extracorporeal treatment of physiological liquids of organism, in particular blood, which avoid the disadvantages of the prior art.

In keeping with these objects and with others which will become apparent hereinafter, one feature of the present invention resides in a device which has means forming a filtration membrane for filtering smaller-size components of a physiological fluid withdrawn from a patient from larger-size components of the same; a bed of particulate adsorbing material with which the smaller-size components are contacted for purification; and means for combining the purified smaller-size components of the fluid with the larger-size components of the fluid for returning the thusly treated fluid to a patient.

In accordance with a specific embodiment of the invention, the device has a housing, means forming a blood inlet for introducing blood into the housing and means forming a blood outlet for withdrawing blood from the housing, means forming a hemofiltration membrane which is accommodated in the housing downstream of the blood inlet and formed so that blood cells substantially pass along the hemofiltration membrane directly to the blood outlet while blood plasma is filtered through the hemofiltration membrane from blood cells and flows into an interior of the housing, and a body of particulate adsorbing material accommodated in the housing and located downstream of the hemofiltration membrane so that the blood plasma separated from the blood cells by the hemofiltration membrane passes through the body of adsorbing material which removes toxins from the blood plasma, and the blood plasma after removal of the toxins flows toward the blood outlet to be mixed with the blood cells to be withdrawn through the blood outlet.

When the device is designed in accordance with the present invention, it removes substantially small molecular weight and middle molecular weight toxin molecules from the physiological fluid of organism and no previous separation of blood is needed into the cell-containing component and liquid-containing component. The separation of the cells from the liquid component was (conventionally) performed in the prior art because if the cells also pass through the charcoal or adsorbing resin material, they would be damaged.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 of the drawings is a view showing a device for purification of physiological liquids of organism in accordance with the present invention.

DESCRIPTION OF PREFERRED EMBODIMENTS

The device has a preferably cone-shaped housing 1 which serves to incorporate both a hemofiltration membrane 2 and a particulate adsorbing material 7. The housing 1 is provided with an upper cup 5 that serves as a blood inlet and a lower cup 6 that serves as a blood outlet. Blood inlet and blood outlet chambers are formed downstream of the inlet and upstream of the outlet correspondingly. The two cups and the housing represent the outer part of the closed device which is intended to be installed into a extracorporeal blood circuit. The device receives the blood from the patient, purifies it from toxic components and returns the blood to the patient. A peristaltic pump or any other device provide the purification device with an appropriate flow of the physiological fluid, and the purification device can be used in combination with a conventional hemodialysis system or without the latter.

The interior of the purification device accomplishes two different processes. The first process is hemofiltration that separates blood sells from plasma. One of possible ways of achieving this goal is using hollow fiber-type membrane with a sufficient permeability. If the pore size of the hemofiltration membrane amounts to 0.1 to 1.0 $\mu$m, the blood cells would remain inside the hollow fiber and would be transported directly from the upper space between the upper cup 5 and the housing 1 toward the lower space between the housing 1 and the lower cup 6. The most preferred pore size of the hollow fiber membrane is 0.4–0.6 $\mu$m. The bundle of the hollow fibers is imbedded into a cylindrical polymeric slab 3 that tightly separates the space between the upper cup 5 and the interior of the housing 1. The opposite end of the hollow fiber bundle is also embedded into a cylindrical polymeric slab 4 of a larger diameter, that, in contract to the slab 3, has a cylindrical opening in the middle. The slab 4 is tightly installed between the housing 1 and the lower cup 6. It, however leaves an access to the interior of the device.

The cone-shaped interior of the device is intended to be filled with particulate absorbing material 7. The latter can be simply introduced into the free space of the device, or, alternatively, be fits packed into a perforated thinwall polymeric cartridge 8. The latter can open the possibility to easily dismantle the device, remove the adsorbing material, regenerate it and reuse in the same manner. In any case, the space filled with the polymer is closed with another round piece 9 that tightly fits into the opening in the polymeric slab 4, and only leaves a central round opening 10 that incorporates a mesh with a plurality of openings of about 50 to 100 $\mu$m. This mesh prevents the adsorbing particles to exit the zone 7.

The device functions as follows. Due to the pressure applied by the blood pump in the inlet part 5 of the device, blood is forced to pass through the hollow fibers toward the outlet part 6. Since the walls of the fibers are porous, major part of plasma escape from the fibers into the interior of the cartridge. Only the blood cells that are too big to diffuse through the membrane are forced to move along the fiber channels toward the outlet end of the device and exit there in a rather concentrated form. The plasma that has left the hollow fibers has no other way to go than through the polymer packing 7 and toward the only available exit 10 in the mes-protected opening in the round piece 9.

There in the space formed by the lower cup 6, plasma is mixed with the blood cells which exit the hollow fiber channels. This lower chamber of the device is provided with a folded insert 11 that introduces turbulence into the flow and provides for better mixing of the plasma and the cells, before they exit the device.

The basic advantage of the device, as compared with conventional hemoprefusion cartridge, is that platelets and blood cells are separated from the adsorbing material. The latter therefore does not need to be extremely hernocompatible, it is sufficient for it to be plasmacompatible. The sorbing material can thus possess a highly active surface for an efficient and rapid removing of various toxins from the plasma.

The simple design of the cartridge permits to keep minimal dead zones of the device and reduce the total volume of the blood required for filling completely the device to an amount of less than 300 ml, preferably to 200 ml. Highly open and active surface of the adsorbing material makes it possible to quickly remove the undesired toxins from the plasma.

Both protein-bonded toxins, and free toxins, including middle-size toxins are efficiently removed. The preferred size of particulate adsorbing material used in the cartridge is between 200 and 900 μm, more preferably, between 300 and 600 μm.

As adsorbing materials useful for the device, many kinds of activated carbon, hypercrosslinked polystyrene adsorbing resins, mesoporous polydivinylbenzene resins, specialty ion exchange resins, as well as any kind of specific affinity sorbents and antibody bearing matrixes can be implied. For these expensive type materials, the possibility of removing from the used cartridge, regeneration and reuse, can be of interest, whereas other nonspecific materials can be used in the form of a disposable cartridge.

The basic idea of the new device, namely combination of the hemofiltration process and plasmaperfusion within one single disposable cartridge, can, naturally be realized with some variations of the construction. For instance, the bundle of hollow fiber membranes device "HFD" can have different number of fibers and different lengths. Normally, the inner diameter of the hollow fiber should amount to 150 to 300 μm, the length between 10 and 100 cm, the internal surface area between 0.1 and 5 sq.m, preferably about 0.5 sq.m. These parameters are selected so as to force about 40 to 70% of the initial blood volume to filtrate through the fiber walls, in the form of plasma. A preferred amount of the filtrate is 50 to 60%. In the case that the hollow fibers 2 are longer that the height of the housing 1, the former should be arranged in the form of a helix along the walls of the housing by a simple rotation of the cylindrical slab 3 with respect to the lower slab 4. In another variant, parallel plate dialyzer "PPD" membrane could be installed instead of the hollowfiber-type membranes. The only essential requirement is that major part of the plasma filtrates from the initial blood through the membrane and then efficiently migrates through the bed of the sorbent material.

The ease of mounting and operating the blood purification device must be of great benefit for emergency situations and treating patients outside a regular hospital. Because of a small flow resistance, the cartridge can also be operated without an external pumping system, by just exploiting the pressure difference between an artery and a vein of a patient, which normally can amount to 50 to 100 Hg mm.

Wherein the device is designed in accordance with the present invention, it basically removes small molecular weight and middle molecular weight toxin molecules from the blood. Depending on the nature of the cartridge packing, the device can also regulate the electrolyte composition of the physiological fluid, as well as release some deficient components or drugs into the liquid. Installing materials with immobilized enzymes, immobilized living cells, or chemically reactive polymers allows conducting chemical transformations on certain components of plasma. Mixed packings of the device that accomplish two or more different tasks, are also feasible.

Though the above presented consideration mainly deals with blood purification, small changes in the construction of the device or certain changes in the parameters of its two basic components, i.e., the membrane and adsorbing material, can open new possibilities to purification or adjusting the composition of other, than blood, physiological fluids, e.g., blood plasma. By changing the size of the pores of the hollow fiber membrane, one can influence the cutoff threshold of the filtration process thus operating in the mode of hemofiltration or plasmafiltration. Indeed, a series of hemocompatible hollow fiber membranes is available with different cutoffs. Well known membranes are F-80 (50,000 m.w. cutoff, Fresenius USA, inc., Walnut Creek, Calif.), Altrex 140 (70,000 m.w. cutoff, Altin Medical, inc. Miami Lakes, Fla.), Plasmaflow (1,000,000 m.w. cutoff, Asahi Medical Co., Ltd. Tokyo, Japan) and others.

It will be understood that each of the elements described above, or two or more together, may also find a useful application in other types of constructions differing from the types described above.

While the invention has been illustrated and described as embodied in device for blood purification, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims:

What is claimed is:

1. A device for extracorporeal treatment of physiological fluids of an organism, comprising means forming a filtration membrane for filtering smeller-size components of a physiological fluid withdrawn from a patient from larger-size components of the said physiological fluid, a bed of particulate porous adsorbing material with which the smaller-size components are contacted for purification: means for combining the purified smaller-size components of the fluid with the larger-size components of the fluid for returning the thusly treated fluid to a patient; an inlet chamber with an inlet; a housing; and an outlet chamber with an outlet said filtration membrane forming means comprising, a plurality of hollow fibers, said hollow fibers and said bed of particulate material being arranged so that said hollow fibers transport the larger-size components of said fluid directly from the inlet chamber into the outlet chamber, while releasing a filtrate of smaller-size components or the fluid into the interior of the housing, and said bed of particulate adsorbing material enabling passage of said filtrate of smaller-size components in the interior of the housing and said filtrate's directly into the outlet chamber without passing again through said hollow fibers, said outlet chamber located wherein a flow of the larger-size components is mixed with a flow of the treated smaller-size components of the physiological fluid before said physiological fluid exits the device and returns to the patient.

2. A device as defined in claim 1, wherein said hollow fibers form hemofiltration membranes, the physiological fluid is blood, the larger-size components of the fluid are blood cells, and the smaller-size components of said fluid is blood plasma.

3. A device as defined in claim 2, wherein said hemofiltration membranes are parallel plate dialyzer membranes.

4. A device as defined in claim 1, wherein said particulate adsorbing material is a material selected from group consisting of activated carbon, hypercrosslinked polystyrene sorbents, macroporous and mesoporous divinylbenzene-styrene copolymers, porous acrylic polymers, immobilized enzymes, immune sorbents, hydrogel-immobilized living hepatic cells, ion-exchanging resins and controlled drug releasing polymers.

5. A device as defined in claim 1, wherein said housing has a conical shape with a cross-section increasing from said inlet to said outlet.

6. A device as defined in claim 1, wherein said bed of adsorbing material has a substantially conical shape which increases in direction from said inlet toward said outlet and is located inside said hemofiltration membrane which has a corresponding inner conical shape for receiving said bed of adsorbing material.

7. A device as defined in claim 1, wherein said membrane is composed of said hollow fibers extending in direction from said inlet to said outlet; and further comprising means for retaining said hollow fibers at two locations spaced from one another in direction from said inlet to said outlet.

8. A device as defined in claim 7, wherein said retaining means includes two retaining polymeric disks arranged so that one of said retaining disks is located adjacent to said inlet and is spaced from the latter so as to form a blood inlet chamber, while the other of said retaining disks is located adjacent to said blood outlet and spaced from the latter so as to form a blood outlet chamber.

9. A device as defined in claim 8, wherein said blood outlet chamber is located between said bed of adsorbing material and said other retaining disk on one hand and said blood outlet on the other hand so that the blood cells and the blood plasma from which toxins are removed is mixed in said outlet chamber.

10. A device as defined in claim 8, wherein said other retaining polymeric disks has a central opening; and further comprising a holding mesh arranged between said bed of particulate material and said outlet for preventing failing of the adsorbent material toward said blood outlet, said holding mesh being located inside said opening of said other retaining disk and having an opening for passing the blood plasma from which toxins are removed.

11. A device as defined in claim 1, wherein said blood outlet chamber is provided with means facilitating intermixing of the blood cells with the blood plasma from which toxins are removed.

12. A device as defined in claim 8, wherein said facilitating means is formed as an insert located in said blood outlet chamber.

13. A device as defined in claim 1; and further comprising a permeable conical element which separates said membrane from said bed of adsorbent material and accommodates said bed of adsorbent material so that said permeable element together with said of adsorbing material can be easily removed.

* * * * *